United States Patent [19]

Kitano et al.

[11] Patent Number: 4,684,476
[45] Date of Patent: Aug. 4, 1987

[54] PYRIMIDINE DERIVATIVE AND LIQUID CRYSTAL COMPOSITION CONTAINING SAME

[75] Inventors: Kisei Kitano; Tetsuya Ogawa; Yoshito Furukawa, all of Yokohamashi; Naoyuki Yoshida, Kamakurashi; Shigeru Sugimori, Fujisawashi; Yasuyuki Goto, Yokohamashi; Toyoshiro Isoyama, Yokohamashi; Kazunori Nigorikawa, Yokohamashi, all of Japan

[73] Assignee: Chisso Corporation, Japan

[21] Appl. No.: 828,338

[22] Filed: Feb. 11, 1986

[30] Foreign Application Priority Data

Feb. 27, 1985 [JP] Japan ................... 60-38328

[51] Int. Cl.⁴ .................... C09K 19/34; C07D 239/00; C07D 239/02
[52] U.S. Cl. ............... 252/299.61; 252/299.5; 350/350 R; 544/242; 544/298; 544/335
[58] Field of Search ............... 252/299.5, 299.61; 350/350 R; 544/298, 335, 242

[56] References Cited

U.S. PATENT DOCUMENTS

| | | | |
|---|---|---|---|
| 3,997,536 | 12/1976 | Boller et al. | 252/299.61 |
| 4,011,173 | 3/1977 | Steinstrasser | 252/299.61 |
| 4,062,798 | 12/1977 | Boller et al. | 252/299.61 |
| 4,311,610 | 1/1982 | Zaschke et al. | 252/299.61 |
| 4,330,426 | 5/1982 | Eidenschine et al. | 252/299.63 |
| 4,358,393 | 11/1982 | Zaschke et al. | 252/299.61 |
| 4,402,849 | 9/1983 | Krause et al. | 252/299.61 |
| 4,505,837 | 3/1985 | Romer et al. | 252/299.5 |
| 4,533,488 | 8/1985 | Fukui et al. | 252/299.61 |
| 4,581,155 | 4/1986 | Goto et al. | 252/299.61 |
| 4,640,795 | 2/1987 | Ogawa et al. | 252/299.61 |

FOREIGN PATENT DOCUMENTS

| | | | |
|---|---|---|---|
| 56501 | 7/1982 | European Pat. Off. | 252/299.61 |
| 84194 | 7/1983 | European Pat. Off. | 252/299.61 |
| 123907 | 11/1984 | European Pat. Off. | 252/299.61 |
| 149238 | 7/1985 | European Pat. Off. | 252/299.61 |
| 2257588 | 6/1973 | Fed. Rep. of Germany | 252/299.61 |
| 144423 | 10/1980 | Fed. Rep. of Germany | 252/299.61 |
| 3315295 | 10/1984 | Fed. Rep. of Germany | 252/299.61 |
| 3404116 | 8/1985 | Fed. Rep. of Germany | 252/299.61 |
| 3407013 | 9/1985 | Fed. Rep. of Germany | 252/299.61 |
| 58-198427 | 11/1983 | Japan | 252/299.63 |
| 59-216876 | 12/1984 | Japan | 252/299.61 |
| 60-54371 | 3/1985 | Japan | 252/299.61 |

OTHER PUBLICATIONS

Lebarny, P. et al., Mol. Cryst. Liq. Cryst., vol. 127, pp. 413–429 (1985).

*Primary Examiner*—Teddy S. Gron
*Attorney, Agent, or Firm*—Leydig, Voit & Mayer

[57] ABSTRACT

A novel pyrimidine derivative which, when used as a component of a liquid crystal composition, is useful for driving a liquid crystal cell containing the composition at low voltages, and a liquid crystal composition containing the same are provided, which pyrimidine derivative is expressed by the formula

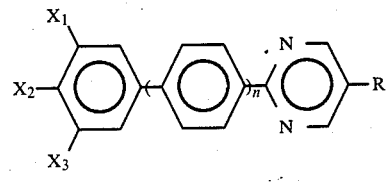

wherein n represents an integer of 0 or 1; R represents an alkyl or alkoxy group of 1 to 10 carbon atoms; and $X_1$, $X_2$ and $X_3$ each represent hydrogen atom, F, Cl or Br as halogeno group, cyano group or trifluoromethyl group and at least one of $X_1$, $X_2$ and $X_3$ is trifluoromethyl group.

4 Claims, No Drawings

PYRIMIDINE DERIVATIVE AND LIQUID CRYSTAL COMPOSITION CONTAINING SAME

BACKGROUND OF THE INVENTION

This invention relates to a novel pyrimidine compound and a liquid crystal composition containing the same.

Liquid crystal substances and their compositions have been used in various display devices by utilizing the dielectric anisotropy value (abbreviated to $\Delta\epsilon$) and the optical anisotropy value (abbreviated to $\Delta n$) thereof in their liquid crystal phases, and their display modes are classified as various types, e.g., TN type (twisted nematic type), DS type (dynamic scattering type), guesthost type, DAP type, etc.

However, for liquid crystal materials used for these display elements there is no single substance which per se may be used to obtain all of the various characteristics such as mesomorphic range, operation voltage, response properties, etc.; thus practically, several kinds of liquid crystal compounds have been mixed together or have been mixed with several kinds of non-liquid crystal compounds to obtain materials which can achieve practical use.

In general, a liquid crystal material having an optional $\Delta\epsilon$ value is obtained by adequately blending those having different $\Delta\epsilon$ values. In order to obtain a liquid crystal composition having a large $\Delta\epsilon$ value, it is necessary to use a component having as large a $\Delta\epsilon$ value as possible, and in this case, such a component is preferred to have a good compatability with other components and also to lower the viscosity of the resulting composition. Further, the liquid crystal material is required to be stable to moisture, light, heat, air, etc. At present, however, there is no single compound which satisfies all of the conditions, but several kinds of liquid crystal compounds have been blended with each other or with compounds similar to liquid crstals, for practical use.

SUMMARY OF THE INVENTION

The object of the present invention is to provide a compound which, when used as a component of a liquid crystal composition, is useful for driving a liquid crystal cell containing the composition at low voltages, and a liquid crystal composition containing the same.

The present invention in a first aspect resides in a pyrimidine derivative expressed by the formula

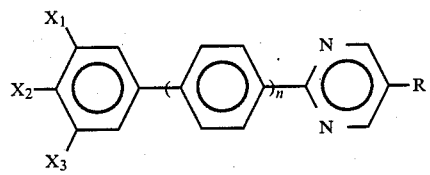

wherein n represents an integer of 0 or 1; R represents an alkyl or alkoxy group of 1 to 10 carbon atoms; and $X_1$, $X_2$ and $X_3$ each represent a hydrogen atom, F, Cl or Br as a halogeno group, cyano group a or a trifluoromethyl group and at least one of $X_1$, $X_2$ and $X_3$ is a trifluoromethyl group.

Further, the present invention in a second aspect resides in a liquid crystal composition comprising at least two components, a first component of which is at least one liquid crystalline compound and a second componenet of which is at least one member of pyrimidine derivatives expressed by the formula (I) set forth in the above first aspect.

DESCRIPTION OF PREFERRED EMBODIMENTS

As preferable compounds of the present invention, pyrimidine compounds expressed by the formulas

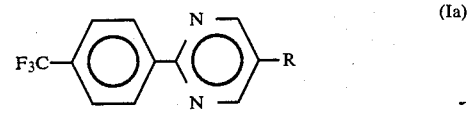 (Ia)

or

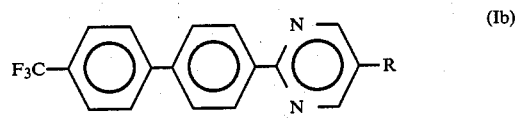 (Ib)

may be mentioned. Beside these compounds, those wherein an H atom at an ortho-position relative to the $CF_3$ group of the formulas (Ia) and (Ib) is replaced by F or a cyano group are also preferred.

Concrete examples of the compounds of the formula (Ia) are as follows:

5-ethyl-2-(4-trifluoromethylphenyl)pyrimidine
5-propyl-2-(4-trifluoromethylphenyl)pyrimidine
5-butyl-2-(4-trifluoromethylphenyl)pyrimidine
5-pentyl-2-(4-trifluoromethylphenyl)pyrimidine
5-hexyl-2-(4-trifluoromethylphenyl)pyrimidine Further, concrete examples of the compounds of the formula (Ib) are as follows:

5-ethyl-2-(4-trifluoromethylbiphenylyl-4')pyrimidine
5-propyl-2-(4-trifluoromethylbiphenylyl-4')pyrimidine
5-butyl-2-(4-trifluoromethylbiphenylyl-4')pyrimidine
5-pentyl-2-(4-trifluoromethylbiphenylyl-4')pyrimidine
5-hexyl-2-(4-trifluoromethylbiphenylyl-4')pyrimidine The compounds of the present invention may be prepared according to the following reaction scheme:

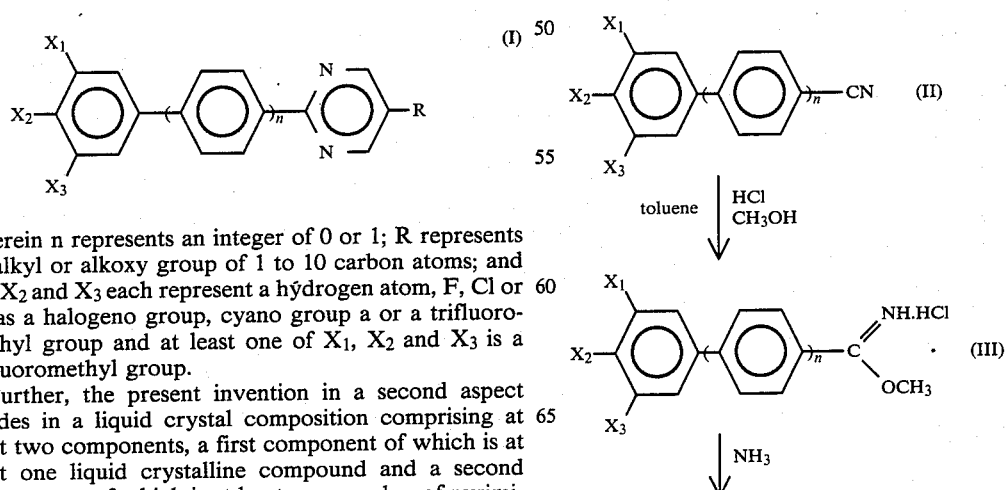

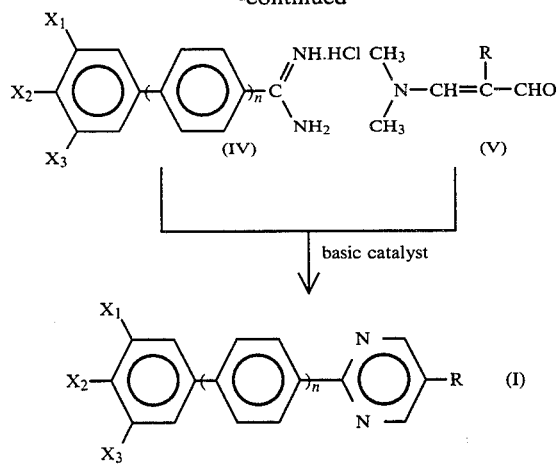

In the above scheme, n represents an integer of 0 or 1; R represents an alkyl group or an alkoxy group each of 1 to 10 carbon atoms; and $X_1$, $X_2$ and $X_3$ each represent a hydrogen atom, F, Cl or Br as a halogen group or trifluoromethyl group; neither of $X_1$, $x_2$ and $X_3$ are cyano group; and at least one of $X_1$, $X_2$ and $X_3$ is trifluoromethyl group.

[Case where none of $X_1$, $X_2$ and $X_3$ is CN group]

In the above scheme, first a nitrile (compound (II)) as a starting raw material is reacted with an alcohol, such as methanol, and HCl gas in toluene solvent to obtain an imido ether hydrochloride derivative (compound (III)), followed by reacting ammonia gas with the compound (III) in an alcohol solvent to obtain an amidine hydrochloride derivative (compound (IV)). This compound (IV) and an acrolein derivative (V) are subjected to a condensation-cyclization reaction in the presence of a suitable basic catalyst such as a metal alcoholate, NaOH, 1,8-diazabicyclo(5.4.0.)-7-undecene, etc. to obtain the objective compound (I).

[Case where either on of $X_1$, $X_2$ and $X_3$ is CN group and the other is Br]

In the case where the compound of formula (I) wherein either one of $X_1$, $X_2$ and $X_3$ is a cyano group and the other is Br, is prepared, a nitrile of the formula (II) wherein $X_1$, $X_2$ or $X_3$ corresponding to the cyano group is an amino group is used as the starting raw material, and after the above condensation-cyclization reaction, the amino group is converted into a diazonium salt with nitrous acid, followed by cyanogenating the salt with cuprous cyanide to obtain the objective compound.

[Case where either one or two of $X_1$, $X_2$ and $X_3$ is (are) CN group]

Further, in the case where the compound of the formula (I) wherein either one or two of $X_1$, $X_2$ and $X_3$ is (are) cyano group and the remainder is not Br, is prepared, a Br-substituted nitrile of the formula (II) wherein $X_1$, $X_2$ or $X_3$ corresponding to the cyano group is Br is used and finally the resulting pyrimidine is cyanogenated with cuprous cyanide to obtain the objective product.

Any of these compounds of the present invention have a superior stability to moisture, light, heat, air, etc., and also have a good compatibility with other liquid crystal compounds such as those of esters, Schiff's bases, azoxy compounds, biphenyls, cyclohexanes, pyrimidines, etc.; hence by blending the former compounds with the latter, it is possible to constitute a liquid crystal composition suitable to various kinds of liquid crystal display elements.

Further the compound of the present invention has a positive large $\Delta\epsilon$ value; hence it is possible to increase the $\Delta\epsilon$ value of liquid crystal compositions obtained by using the compound as a component thereof, and it is also possible to reduce the driving voltage of liquid crystal cells using the compositions.

The compound of the present invention of the formula (I) wherein n=0 has a low viscosity; hence it is possible to reduce the driving voltage and improve the response properties of liquid crystal cells wherein liquid crystal compositions containing the compoud as a component thereof are used.

The compound of the formula (I) wherein n=1 has a high clearing point; hence when the compound is used as a component, it is possible to obtain a liquid crystal composition having the upper limit of its mesomorphic range broadened without raising its viscosity so much.

The composition of the present invention is characterized in comprising at least two components, a first component of which is at least one liquid crystal compound and a second component of which is at least one pyrimidine derivative expressed by the above-mentioned formula (I).

Examples of liquid crystal compounds used as a component of the composition of the present invention are those of Schiff's bases, azoxy compounds, biphenyls, cyclohexanes, esters, pyrimidines, dioxanes, etc.

The content of the compound of the formula (I) in the composition of the present invention varies depending on the kinds and contents of other liquid crystal components and non-liquid crystal components and further the number of homologues of the compound of the formula (I) used. When a single compound is used as the compound of the formula (I), is content is usually in the range of 1 to 30% by weight, while when a few homologues of the compound of the formula (I) are blended and used, the content can be further increased.

When the compound of the formula (I) is blended with liquid crystal compounds of cyanophenylcyclohexanes, a blend consisting of 5 to 20% by weight of the former and 80 to 95% by weight of the latter is preferred.

The present invention will be described in more detail by way of Examples, but it should not be construed to be restricted thereto.

EXAMPLE 1

5-Propyl-2-(4-trifluoromethylphenyl)pyrimidine

4-Trifluoromethylbenzamidine hydrochloride (5 g, 0.02 mol) and α-propyl-β-dimethylaminoacrolein (3 g, 0.02 mol) were added to a sodium methylate solution having metallic sodium (1 g) dissolved in anhydrous methanol (50 ml), followed by boiling the mixture for 4 hours with stirring, distilling off methanol, adding toluene (50 ml) to the reaction residue to extract the product, washing the resulting extract with water, drying the toluene layer with anhydrous sodium sulfate, distilling off toulene and three times recrystallizing the residue from methanol to obtain 5-propyl-2-(4-trifluoromethylphenyl)pyrimidine (3 g, 0.01 mol).

The values of the elemental analysis of this compound accorded well with the theoretical values as follows:

| Element | Observed value | Theoretical value |
|---|---|---|
| C | 63.1% | 63.15% |
| H | 4.9% | 4.92% |
| N | 10.5% | 10.52% |
| F | 21.4% | 21.41% |

This compound had a m.p. of 89° C.

Further, the $\Delta\epsilon$ value, $\Delta n$ value and viscosity at 20° C. of this compound were sought by extrapolation from the values of the physical properties of a blend of this compound with a liquid crystal composition of phenylcyclohexanes. The $\Delta\epsilon$ and $\Delta n$ were 37 and 0.07, respectively. The viscosity at 20° C. ($\eta_{20}$) of the compound was 15 cp.

EXAMPLES 2~16

Compounds prepared in the same manner as in Example 1 and their phase transition points and the values of the physical properties of the compounds sought by extrapolation from blends of the compounds with liquid crystals of phenylcyclohexanes are shown in Table 1 together with the results of Example 1.

TABLE 1

| | In formula (I) | | | | Phase transition point (°C.) | | | | $\eta_{20}$ | |
|---|---|---|---|---|---|---|---|---|---|---|
| Example | $X_1$ | $X_2$ | $X_3$ | n | R | C | S | I | $\Delta n$ | (cP) | $\Delta\epsilon$ |
| 1 | H | $F_3C$ | H | 0 | $C_3H_7$ | • | 89 — | • | 0.07 | 15 | 37 |
| 2 | H | $F_3C$ | H | 0 | $C_2H_5$ | • | 87 — | • | 0.08 | 11 | 40 |
| 3 | H | $F_3C$ | H | 0 | $C_4H_9$ | • | 49 (• 32) | • | 0.07 | 24 | 31 |
| 4 | H | $F_3C$ | H | 0 | $C_5H_{11}$ | • | 50 (• 41) | • | 0.08 | 24 | 36 |
| 5 | H | $F_3C$ | H | 0 | $C_6H_{13}$ | • | 45 (• 30) | • | 0.07 | 29 | 25 |
| 6 | H | $F_3C$ | H | 0 | $OCH_3$ | • | 125 — | • | 0.06 | 41 | 35 |
| 7 | $F_3C$ | H | $F_3C$ | 0 | $C_2H_5$ | • | 77 — | • | | | |
| 8 | $F_3C$ | H | $F_3C$ | 0 | $C_3H_7$ | • | 48 — | • | | | |
| 9 | $F_3C$ | H | $F_3C$ | 0 | $C_4H_9$ | • | 35 — | • | | | |
| 10 | $F_3C$ | H | $F_3C$ | 0 | $C_5H_{11}$ | • | 28 — | • | | | |
| 11 | $F_3C$ | H | $F_3C$ | 0 | $C_6H_{13}$ | • | 21 — | • | | | |
| 12 | H | $F_3C$ | H | 1 | $C_2H_5$ | • | 156 • 254 | • | 0.20 | 33 | 43 |
| 13 | H | $F_3C$ | H | 1 | $C_3H_7$ | • | 173 • 240 | • | 0.22 | 38 | 41 |
| 14 | H | $F_3C$ | H | 1 | $C_4H_9$ | • | 129 • 230 | • | 0.19 | 43 | 32 |
| 15 | H | $F_3C$ | H | 1 | $C_5H_{11}$ | • | 128 • 228 | • | 0.20 | 40 | 34 |
| 16 | H | $F_3C$ | H | 1 | $C_6H_{13}$ | • | 134 • 222 | • | 0.19 | 52 | 29 |

In the column of phase transition point of Table 1, C, S and I represent crystalline phase, smectic phase and isotropic liquid phase, respectively. The values inside the parenthese () represent monotropic transition points.

EXAMPLE 17

A liquid crystal composition A consisting of $C_3H_7$—⟨H⟩—⟨O⟩—CN    24 parts by weight, $C_5H_{11}$—⟨H⟩—⟨O⟩—CN    36 parts by weight, $C_7H_{15}$—⟨H⟩—⟨O⟩—CN    25 parts by weight and $C_5H_{11}$—⟨H⟩—⟨O⟩—⟨O⟩—CN    15 parts by weight had a N-I point (nematic-clearing point) of 72.0° C., a $\eta_{20}$ (viscosity at 20° C.) of 27.8 cp, a $\Delta\epsilon$ of 11.6 ($\epsilon_{//}=16.1$, $\epsilon_{\perp}=4.5$) and a $\Delta n$ (optical anisotrophy) of 0.140 ($n_e=1.632$, $n_0=1.492$), and when this compostion was sealed in a TN cell of 10 μm thick, the threshold voltage and saturation voltage were 1.75 V and 2.40 V, respectively.

When 5-ethyl-2-(4-trifluoromethylphenyl)pyrimidine, prepared in Example 2 (a compound of the present invention) (15 parts by weight) was added to the above liquid crystal composition A (85 parts by weight), the resulting liquid crystal composition had a N-I point of 56.5° C. and a $\Delta n$ of 0.131, and the $\eta_{20}$ notably lowered down to 25.3 cp, the $\Delta\epsilon$ greatly rose up to 15.8 ($\epsilon_{//}=21.5$, $\epsilon_{\perp}=5.7$) and the threshold voltage were and saturation voltage notably lowered to 1.34 V and 1.71 V, respectively.

EXAMPLE 18

A liquid crystal composition was prepared which consisted of 85 parts by weight of the above liquid crystal composition A used in Example 17 and 15 parts by weight of 5-hexyl-2-(4-trifluoromethylphenyl)-pyrimidine prepared in Example 5. This composition had a N-I point of 56.6° C., a $\Delta n$ of 0.130, a $\eta_{20}$ of 28.0 cp and a $\Delta\epsilon$ of 13.6 ($\epsilon_{//}=18.9$, $\epsilon_{\perp}=5.3$). Further, the threshold voltage and saturation voltage of the liquid crystal cell measured in the same manner as in Example 17 were 1.41 V and 1.81 V, respectively.

EXAMPLE 19

A liquid crystal composition B consisting of $C_3H_7$—⟨H⟩—⟨O⟩—CN    30 parts by weight, $C_5H_{11}$—⟨H⟩—⟨O⟩—CN    40 parts by weight and $C_7H_{15}$—⟨H⟩—⟨O⟩—CN    30 parts by weight had a N-I point of 52.1° C., a $\eta_{20}$ of 23.4 cp, a $\Delta\epsilon$ of 11.2 ($\epsilon_{//}=15.9$, $\epsilon_{\perp}=4.7$), and a $\Delta n$ of 0.119 ($n_e=1.609$, $n_o=1.490$), and when this composition was sealed in a TN cell of 10 μm thick, the threshold voltage and saturation voltage were 1.54 V and 2.13 V, respectively.

When 5-pentyl-2-(4-trifluoromethylbiphenylyl-4')pyrimidine prepared in Example 15 (a compound of the present invention) (15 parts by weight) was added to the above liquid crystal composition B (85 parts by weight), the N-I point of the resulting liquid crystal composition rose to 56.4° C., the $\Delta n$ rose to 0.127, the $\eta_{20}$ was 25.1 cp, the $\Delta \epsilon$ notably rose to 13.5 ($\epsilon_{//}=18.8$, $\epsilon_{\perp}=5.3$) and the threshold voltage and saturation voltage were lowered to 1.53 and 2.05 V, respectively.

What we claim is:

1. A pyrimidine compound expressed by the formula

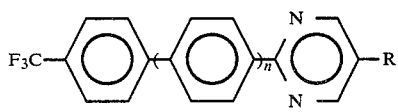

wherein n represents an integer of 0 or 1 and R represents an alkyl or alkoxy group of 1 to 10 carbon atoms.

2. A pyrimidine derivative according to claim 1 expressed by the formula

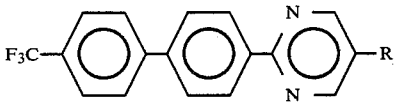

wherein R represents an alkyl or alkoxy group of 1 to 10 carbon atoms.

3. A pyrimidine derivative according to claim 1 expressed by the formula

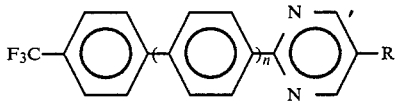

wherein R represents an alkyl or alkoxy group of 1 to 10 carbon atoms.

4. A liquid crystal composition comprising at least two components, a first component including at least one liquid crystalline compound and a second component including at least one pyrimidine compound expressed by the formula

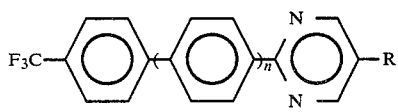

wherein n represents an integer of 0 or 1 and R represents an alkyl or alkoxy group of 1 to 10 carbon atoms.

* * * * *